(12) United States Patent
Taylor et al.

(10) Patent No.: US 6,841,554 B2
(45) Date of Patent: Jan. 11, 2005

(54) CRYSTALLINE SALTS OF 7-[4-(4-FLUOROPHENYL)-6-ISOPROPYL-2-[METHYL(METHYLSULFONYL)AMINO]PYRIMIDIN-5-YL]-(3R,5S)-3,5-DIHYDROXYHEPT-6-ENOIC ACID

(75) Inventors: Nigel Philip Taylor, Macclesfield (GB); Tetsuo Okada, Osaka (JP)

(73) Assignees: AstraZeneca AB, Sodertalje (SE); Shionogi & Co., Ltd., Osaka (JP)

( * ) Notice: Subject to any disclaimer, the term of this patent is extended or adjusted under 35 U.S.C. 154(b) by 94 days.

(21) Appl. No.: 10/203,890

(22) PCT Filed: Feb. 12, 2001

(86) PCT No.: PCT/GB01/00574
§ 371 (c)(1),
(2), (4) Date: Aug. 15, 2002

(87) PCT Pub. No.: WO01/60804
PCT Pub. Date: Aug. 23, 2001

(65) Prior Publication Data
US 2003/0045718 A1 Mar. 6, 2003

(30) Foreign Application Priority Data
Feb. 15, 2000 (GB) .............................................. 0003305

(51) Int. Cl.[7] ...................... C07D 239/38; A61K 21/505
(52) U.S. Cl. ........................................ 514/275; 544/297
(58) Field of Search .......................... 514/275; 544/297, 544/332

(56) References Cited

U.S. PATENT DOCUMENTS

| | | | |
|---|---|---|---|
| 4,294,846 A | 10/1981 | Albers-Schonberg et al. .... | 514/460 |
| 4,319,039 A | 3/1982 | Albers-Schonberg ....... | 560/256 |
| 4,647,659 A | 3/1987 | Cook et al. .................. | 540/345 |
| 4,681,893 A | 7/1987 | Roth .......................... | 514/422 |
| 4,868,185 A | 9/1989 | Chuckolowski et al. | |
| 4,940,727 A | 7/1990 | Inamine et al. .............. | 514/460 |
| 5,177,080 A | 1/1993 | Angerbauer et al. | |
| 5,223,415 A | 6/1993 | Conder et al. ............... | 435/125 |
| 5,369,123 A | 11/1994 | Santafianos et al. | |
| 5,385,929 A | 1/1995 | Bjorge et al. ................ | 514/422 |
| 5,403,860 A | 4/1995 | Kurabayashi et al. ....... | 514/460 |
| 6,316,460 B1 | 11/2001 | Creekmore et al. ......... | 514/275 |

FOREIGN PATENT DOCUMENTS

| | | |
|---|---|---|
| EP | 0 026 044 | 4/1981 |
| EP | 0 065 835 | 12/1982 |
| EP | 0 211 416 B1 | 2/1987 |
| EP | 0 247 633 B1 | 12/1987 |
| EP | 0 326 388 A2 | 8/1989 |
| EP | 0 409 281 B1 | 1/1991 |
| EP | 0 456 214 A1 | 11/1991 |
| EP | 0 463 456 A1 | 1/1992 |
| EP | 0 520 406 B1 | 12/1992 |
| EP | 0 330 172 B1 | 6/1994 |
| EP | 0 658 550 A2 | 6/1995 |
| FR | 2 795 324 A | 12/2000 |
| GB | 2 073 199 A | 10/1981 |
| WO | 93/25557 | 12/1993 |
| WO | 96/33197 | 10/1996 |
| WO | 97/18216 | 5/1997 |
| WO | 97/03959 | 6/1997 |
| WO | 00/17150 | 3/2000 |
| WO | 00 42024 A | 7/2000 |
| WO | 00/45817 | 8/2000 |
| WO | 00/45818 | 8/2000 |
| WO | 00/45819 | 8/2000 |
| WO | 00/49014 | 8/2000 |
| WO | 01 04100 A | 1/2001 |
| WO | 01/54668 A1 | 8/2001 |
| WO | 01/54669 A1 | 8/2001 |

OTHER PUBLICATIONS

Watanabe et al.; "Synthesis and Biological Activity of Methanesulfonamide Pyrimidine–and N–Methanesulfonyl Pyrrole–Substituted 3,5–Dihydroxy–6–Heptenoates, a Novel Series of HMG–COA Reductase Inhibitors", Bioorganic & Medicinal Chemistry, GB. Elsevier Science LTD., vol. 5, No. 2, 1997, pp. 437–444, XP000882043.

Sato et al., "X–Ray Crystal Structure of the tert–Octylamine Salt (RMS–431) of Pravastatin", The Journal of Antibiotics, vol. XLI, No. 9, 1988, pp. 1265–1267.

Lee et al., "Process Development: Fine Chemicals from Grams to Kilograms", Oxford Chemistry Primers, Oxford University Press, 1995.

*Primary Examiner*—Thomas McKenzie
(74) *Attorney, Agent, or Firm*—Morgan, Lewis & Bockius LLP

(57) ABSTRACT

The invention relates to crystalline salts of the compound (E)-7-[4-(4-fluorophenyl)-6-iso-propyl-2-[methyl(methylsulfonyl)amino]pyrimidin-5-yl]-(3R,5S)-3,5-dihydroxyhept-6-enoic acid of formula (I), as well as processes for their manufacture, pharmaceutical compositions containing them, and their uses (I)

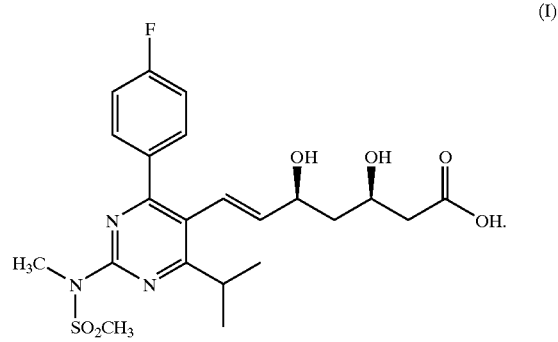

12 Claims, 9 Drawing Sheets

CRYSTALLINE SALTS OF 7-[4-(4-FLUOROPHENYL)-6-ISOPROPYL-2-[METHYL(METHYLSULFONYL)AMINO]PYRIMIDIN-5-YL]-(3R,5S)-3,5-DIHYDROXYHEPT-6-ENOIC ACID

The present invention relates to pyrimidine derivatives, and more particularly to novel crystalline salts of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid of the formula

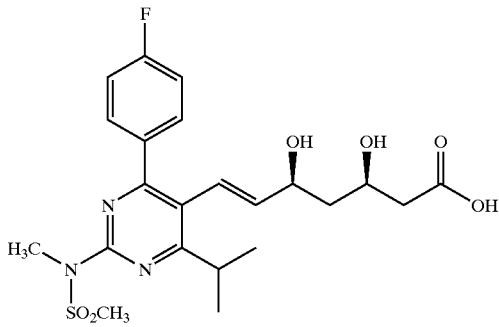

which are useful as inhibitors of the enzyme 3-hydroxy-3-methylglutaryl-coenzyme A reductase (HMG CoA reductase) and as intermediates in the manufacture of, for example, the non-crystalline calcium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid of the formula

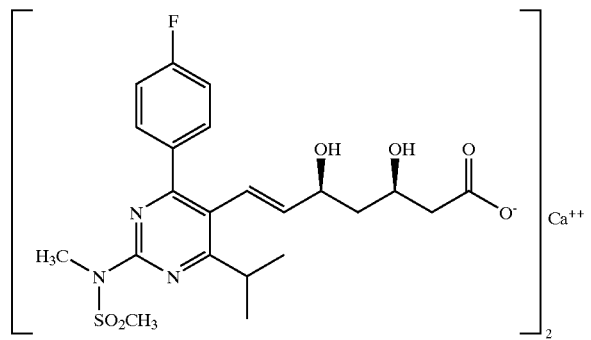

The invention also concerns pharmaceutical compositions which include the crystalline salts, as well as processes for the manufacture of the crystalline salts. The invention further concerns methods of treating medical conditions in which HMG CoA reductase is implicated using the crystalline salts, for example hyperlipidemia, hypercholesterolemia and atherosclerosis, and the use of the crystalline salts in the manufacture of a medicanent. The invention further concerns the use of the crystalline salts in the manufacture of the non-crystalline calcium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid.

European Patent Application, Publication No. 521471 (hereinafter EPA 521471), discloses an amorphous (powder) form of the calcium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid, and the sodium salt is obtained therein as "powdery crystals". These salts are HMG CoA reductase inhibitors and the calcium salt is undergoing clinical trials.

A powdery or amorphous form of a compound intended for pharmaceutical use may give rise to manufacturing problems and there is therefore a need to identify alternative salts of (E)-7-[4-(4-fluorophenyl)-6-isopropyl-2-[methyl (methylsulfonyl)amino]pyrimidin-5-yl]-(3R,5S)-3,5-dihydroxyhept-6-enoic acid which are crystalline. Such crystalline salts can generally be purified more easily than an amorphous form and may possess other advantageous properties, for example in relation to their particular crystalline form and/or their solubility characteristics and/or their lack of hygroscopicity and/or their stability characteristics, including their thermal stability properties and/or their ability to undergo oxidative degradation. A difficulty is also experienced in obtaining pure amorphous calcium salt using the procedure disclosed in EPA 521471, because of the difficulty in purification of the precursor sodium salt arising from its physical form. A further feature of the crystalline salts is that they can also advantageously be used as intermediates in the manufacture of the non-crystalline calcium salt, to enable isolation of non-crystalline calcium salt with a purity level and uniformity suitable for formulation to meet exacting pharmaceutical requirements and specifications.

We have now discovered novel crystalline salts of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid, which provide a basis for the present invention.

According to the invention there is provided a crystalline salt of the compound (E)-7-[4-(4-fluorophenyl)-6-isopropyl-2-[methyl(methylsulfonyl)amino]pyrimidin-5-yl]-(3R,5S)-3,5-dihydroxyhept-6-enoic acid, wherein the salt is an ammonium ($NH_4^+$), methylammonium ($CH_3NH_3^+$), ethylammonium ($CH_3CH_2NH_3^+$), diethanolammonium [$(HOCH_2CH_2)_2NH_2^+$], tris(hydroxymethyl) methylammonium [$(HOCH_2)_3CNH_3^+$], benzylammnonium ($C_6H_5CH_2NH_3^+$), 4-methoxybenzylammonium (4-$CH_3O$—$C_6H_5CH_2NH_3^+$), lithium ($Li^{30}$) or magnesium ($Mg^{2+}$) salt.

BRIEF DESCRIPTION OF DRAWINGS

The crystalline salts of the invention are described in the Examples hereinafter. Independent aspects of the invention comprise:

(1) a crystalline ammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=12.9, 15.2, 18.0, 18.2, 18.5, 20.2, 22.4, 23.0, 24.0 and 27.2°, as shown in FIG. 1;

Figure 2:
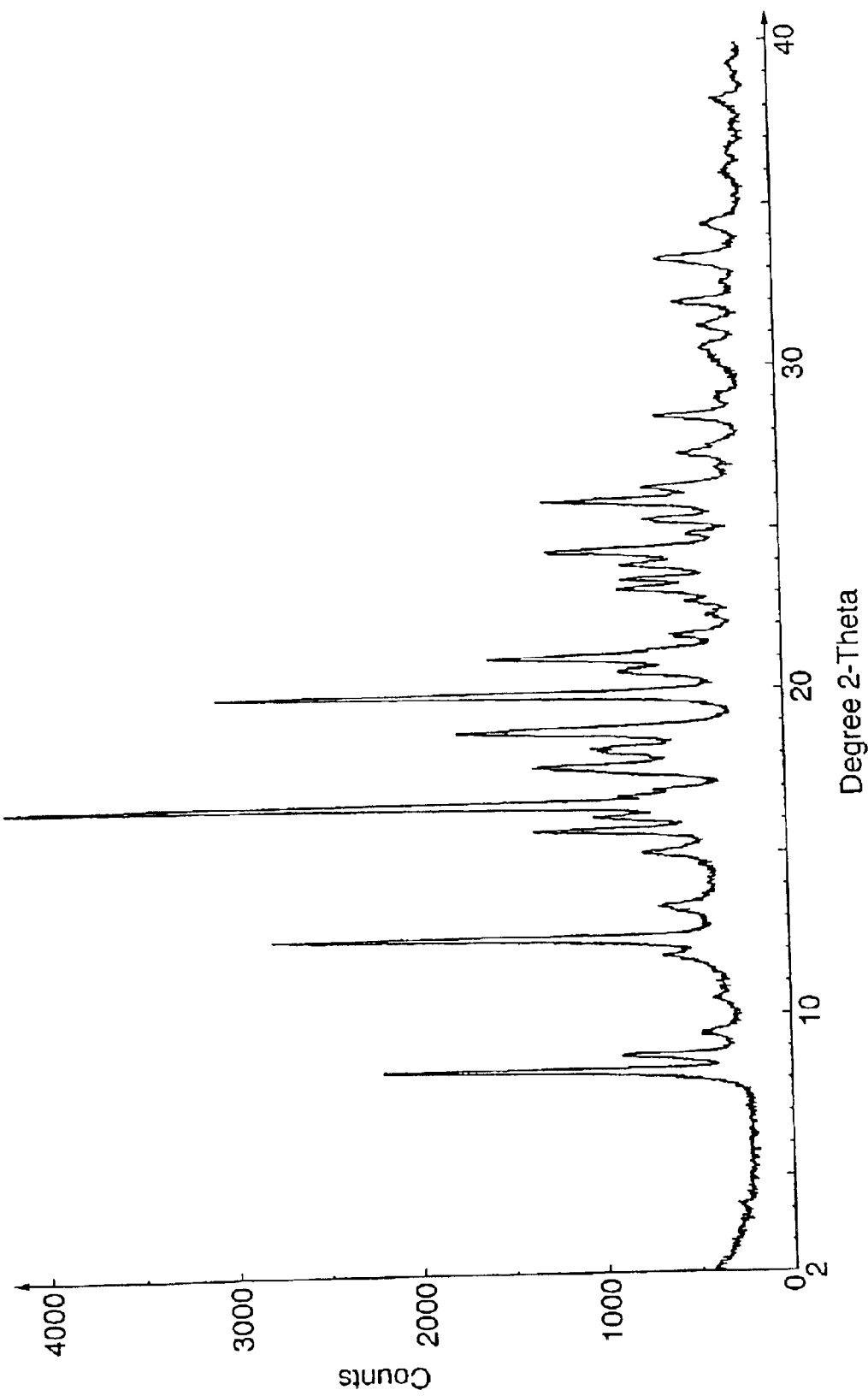
Figure 3:
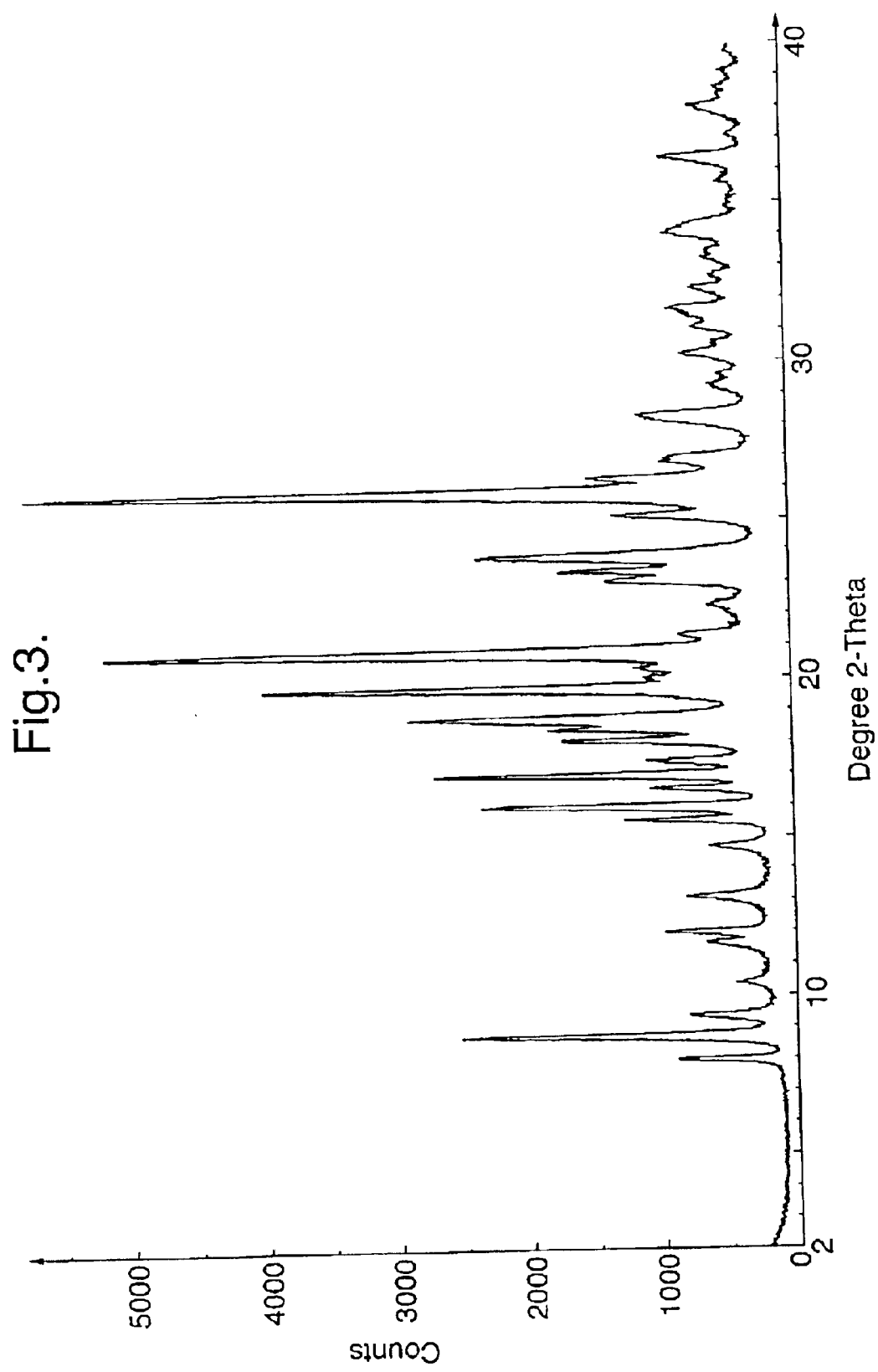
Figure 4:
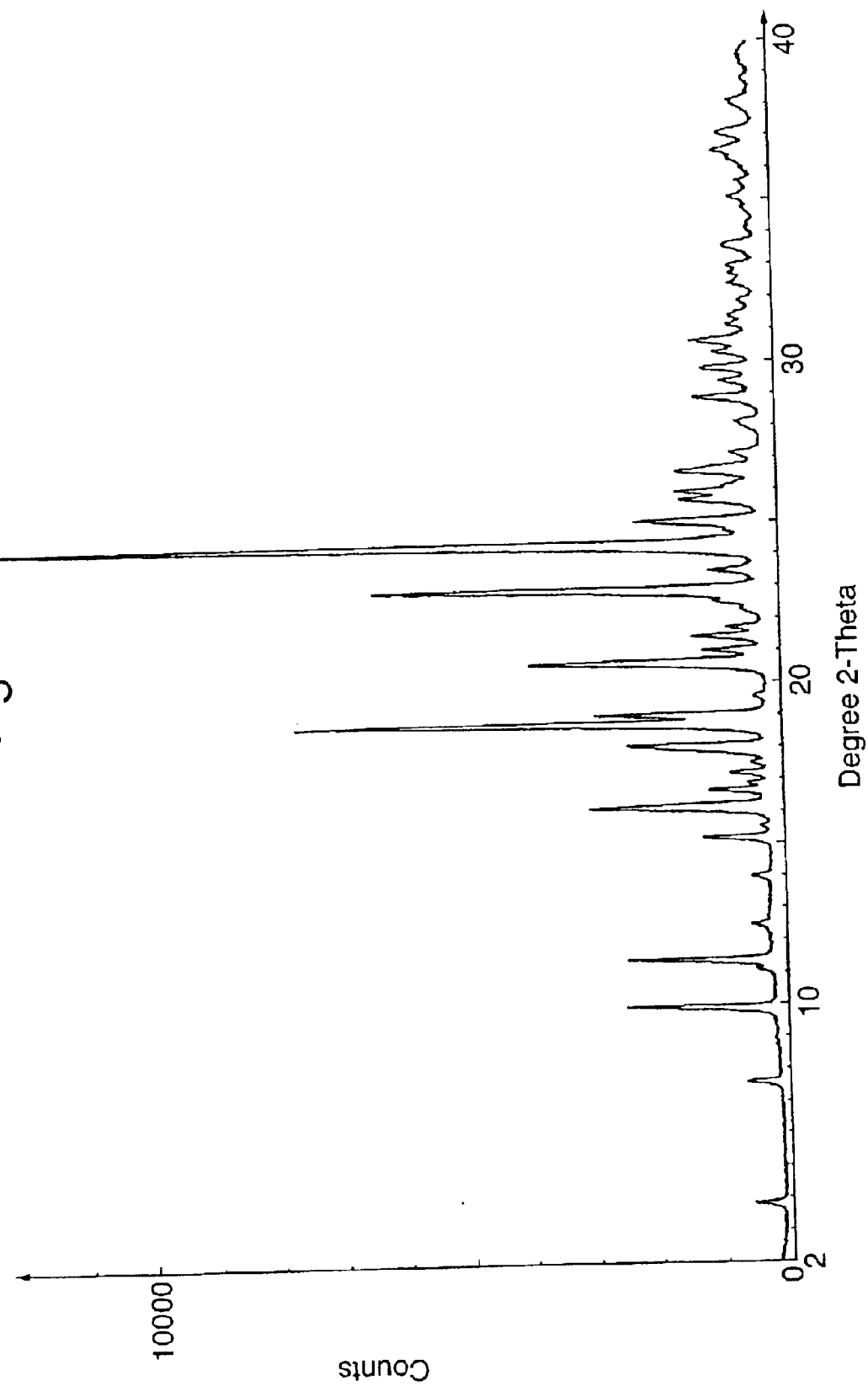
Figure 5:
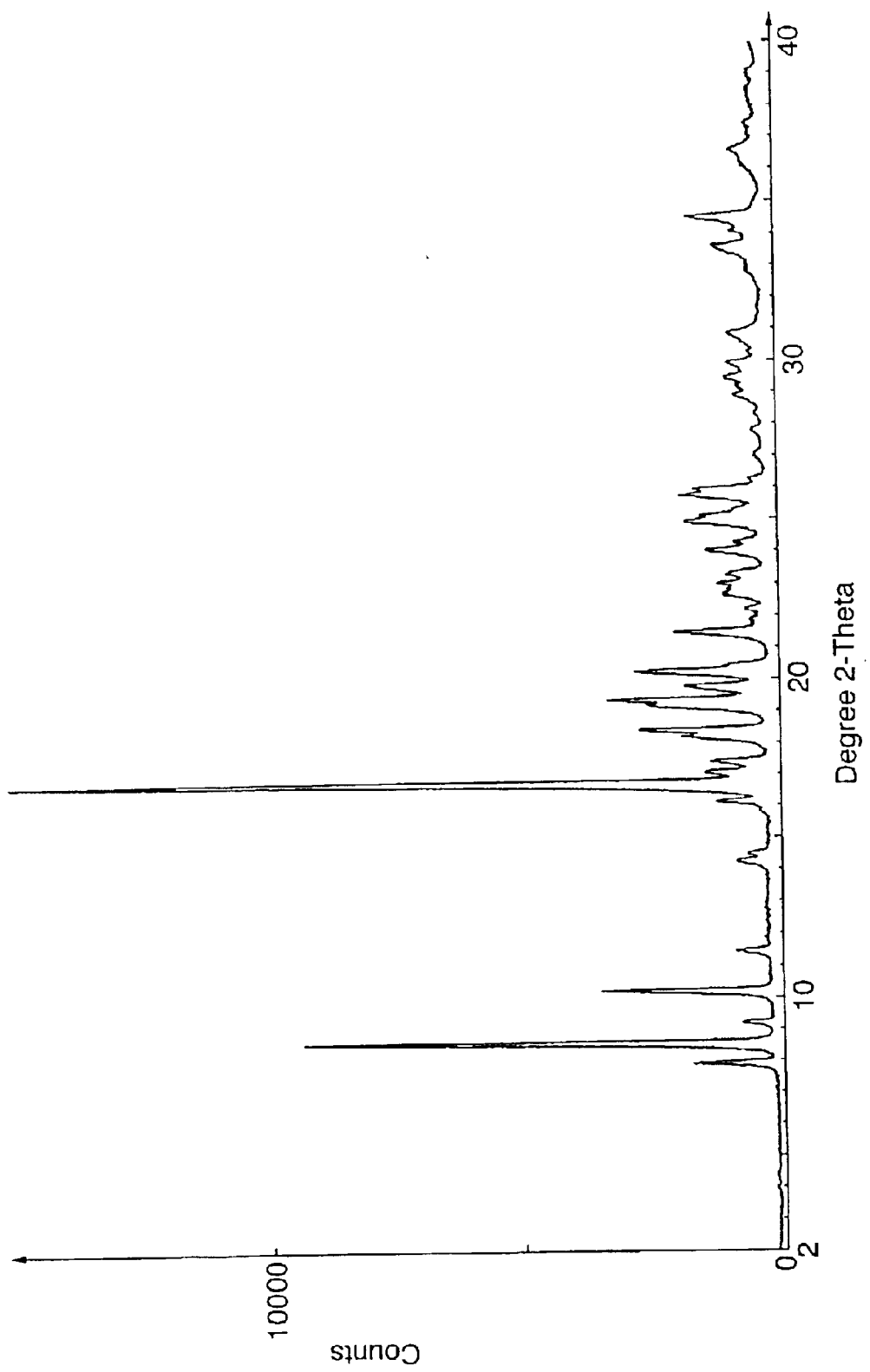
Figure 6:
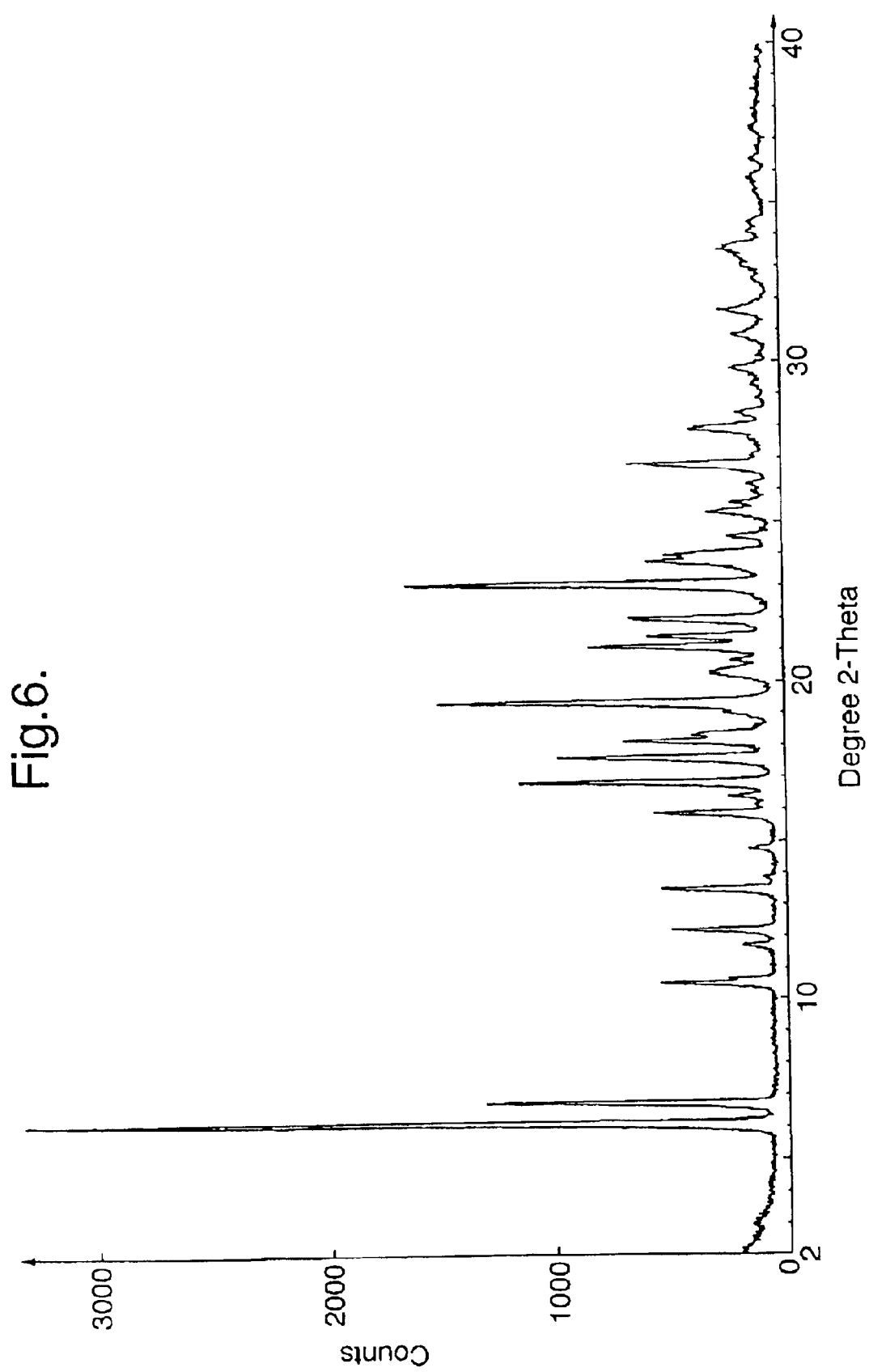
Figure 7:
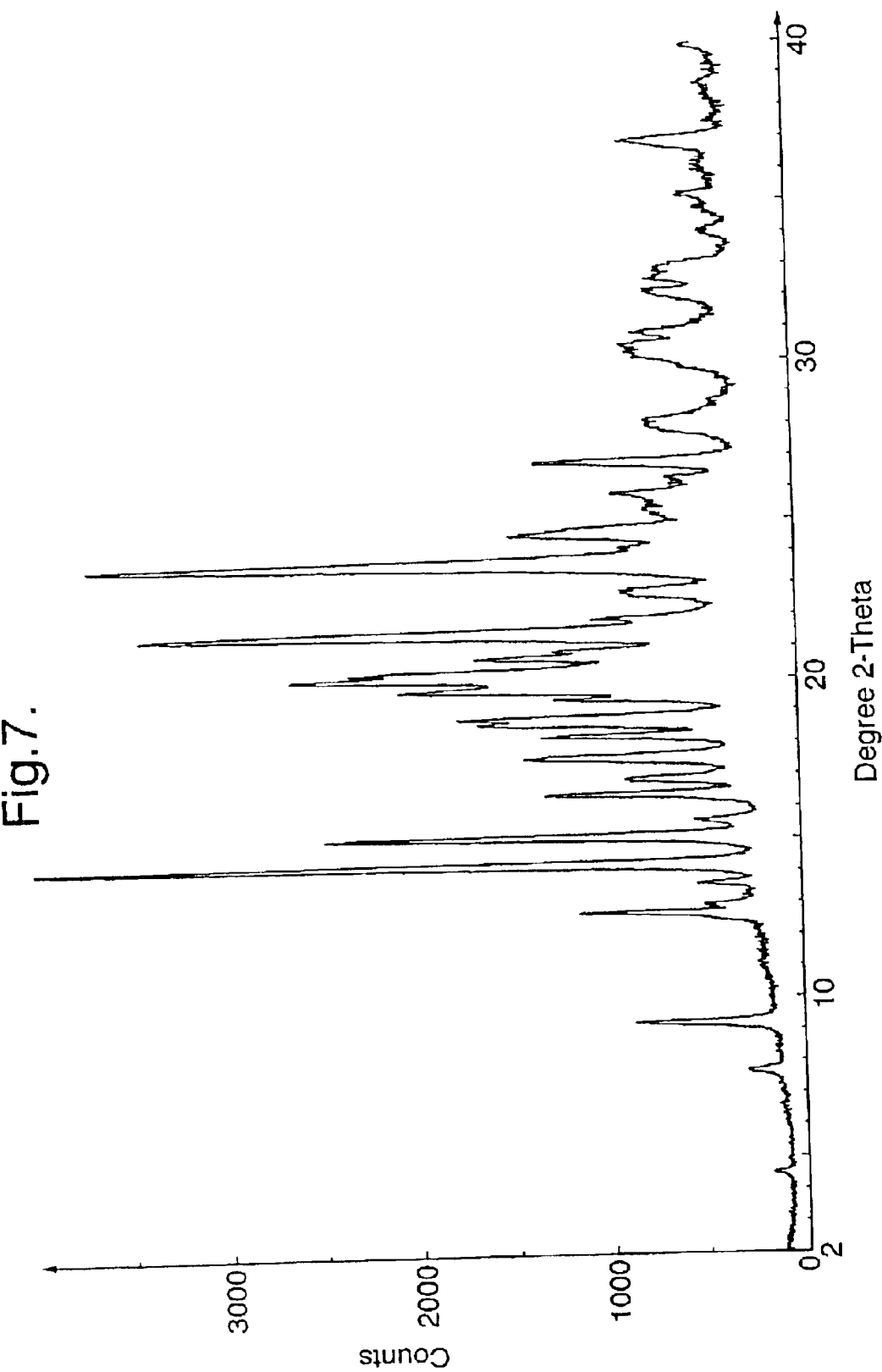
Figure 8:
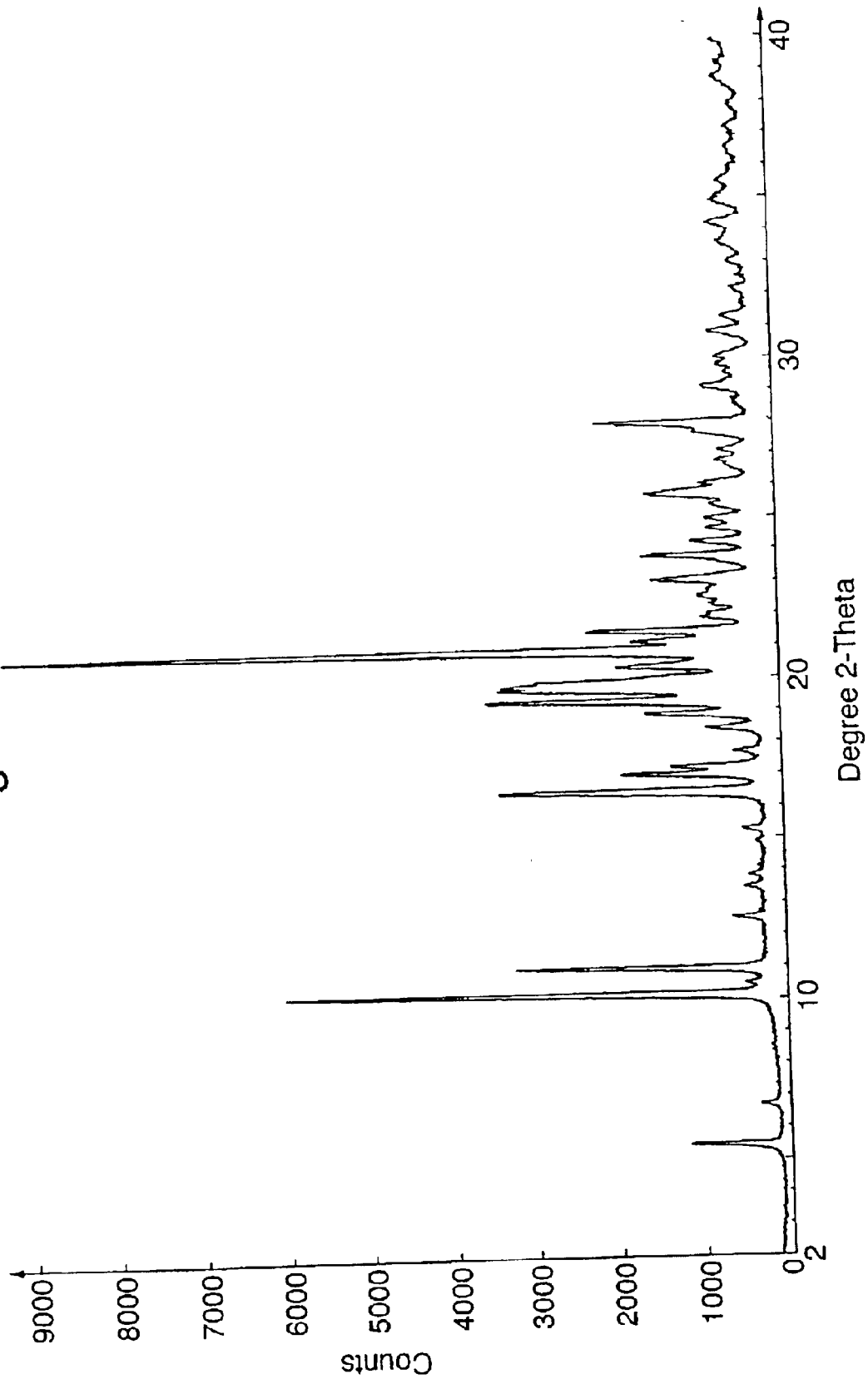
Figure 9:
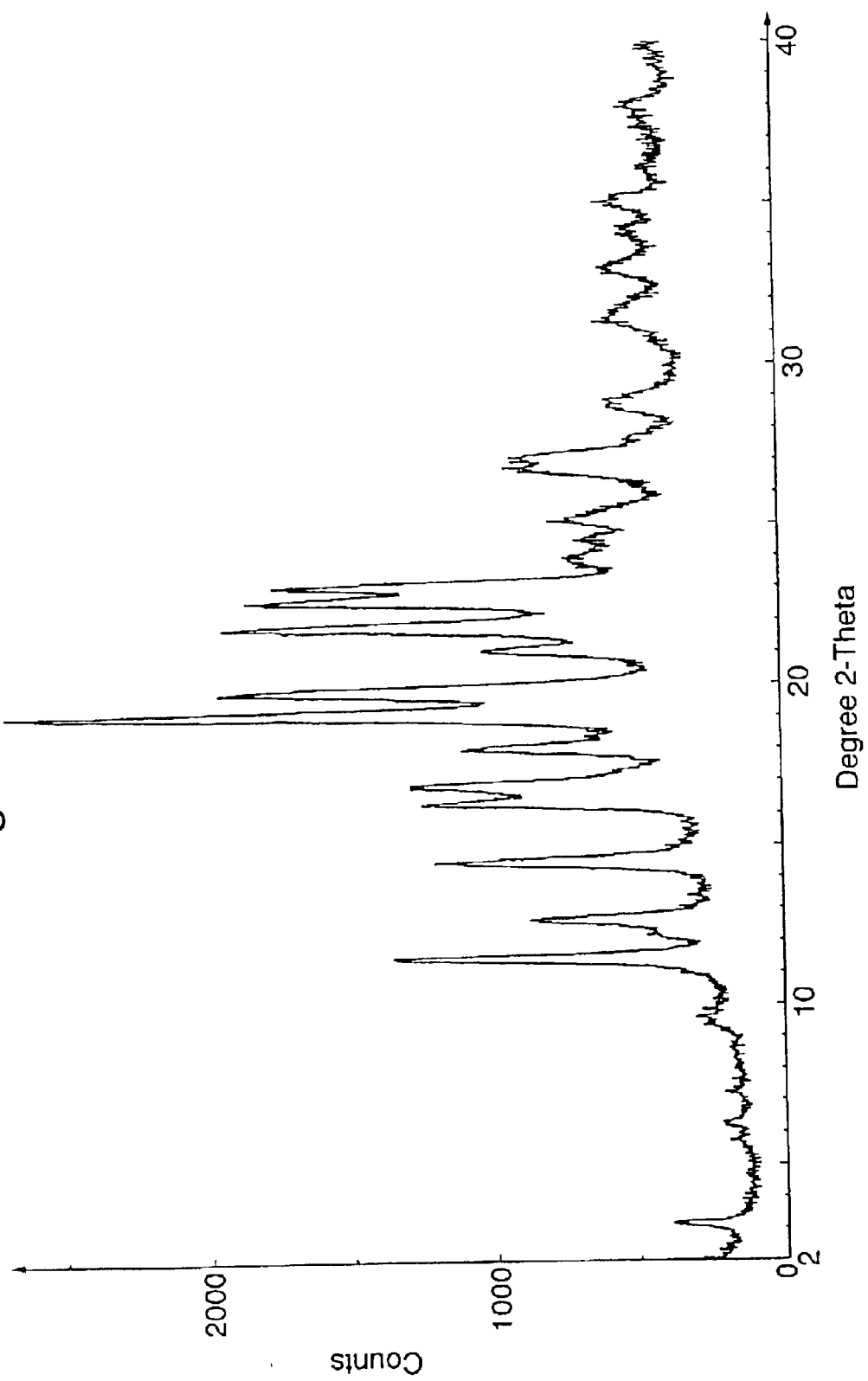

(2) a crystalline methylammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=8.2, 12.3, 15.7, 16.5, 17.6, 18.7, 19.9, 21.0, 24.3 and 25.9°, as shown in FIG. 2;

(3) a crystalline ethylammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=8.6, 15.9, 16.9, 18.4, 18.7, 19.7, 20.8, 23.3, 23.8 and 25.8°, as shown in FIG. 3;

(4) a crystalline diethanolammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=9.9, 11.4, 16.1, 18.0, 18.7, 19.0, 20.6, 22.9, 24.3 and 25.0°, as shown in FIG. 4;

(5) a crystalline tris(hydroxymethyl)methylammonium salt of (E)-7-[4-(4-fluorophenyl)-6-isopropyl-2-[methyl (methylsulfonyl)amino]pyrimidin-5-yl]-(3R,5S)-3,5-dihydroxyhept-6-enoic acid having an X-ray powder diffraction pattern with specific peaks at 2-theta=7.9, 8.5, 10.2, 16.7, 18.4, 19.3, 19.8, 20.2, 21.5 and 24.9°, as shown in FIG. 5;

(6) a crystalline benzylammonium salt of (E)-7-[4-(4-fluorophenyl)-6-isopropyl-2-[methyl(methylsulfonyl) aminopyrimidin-5-yl]-(3R,5S)-3,5-dihydroxyhept-6-enoic acid having an X-ray powder diffraction pattern with specific peaks at 2-theta=6.1, 6.7, 16.8, 17.6, 18.1, 19.3, 21.1, 21.9, 23.0 and 26.8°, as shown in FIG. 6;

(7) a crystalline 4-methoxybenzylammonium salt of (E)-7-[4-(4-fluorophenyl)-6-isopropyl-2-[methyl (methylsulfonyl)amino]pyrimidin-5-yl]-(3R,5S)-3,5-dihydroxyhept-6-enoic acid having an X-ray powder diffraction pattern with specific peaks at 2-theta=14.2, 15.1, 17.5, 18.8, 19.7, 20.1, 20.7, 21.5, 23.7 and 24.5°, as shown in FIG. 7;

(8) a crystalline lithium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=10.2, 11.0, 16.4, 17.0, 19.3, 19.8, 20.4, 20.9, 21.5 and 28.0°, as shown in FIG. 8; and (9) a crystalline magnesium salt of (E)-7-[4-(4-fluorophenyl)-6-isopropyl-2-[methyl(methylsulfonyl) amino]pyrimidin-5-yl]-(3R,5S)-3,5-dihydroxyhept-6-enoic acid having an X-ray powder diffraction pattern with specific peaks at 2-theta=11.5, 14.5, 16.3, 16.8, 18.0, 19.1, 19.8, 21.8, 22.6 and 23.0°, as shown in FIG. 9.

The crystalline tris(hydroxymethyl)methylammonium salt described above is a particularly preferred crystalline salt having particularly advantageous physical characteristics, for example it has advantageous thermal properties, it is non-hygroscopic and it possesses an advantageous solubility profile.

The X-ray powder diffraction spectra were determined by mounting a sample of the crystalline salt on Siemens single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated X-ray source was passed through an automatic variable divergence slit set at V20 and the reflected radiation directed through a 2 mm antiscatter slit and a 0.2 mm detector slit. The sample was exposed for 4 seconds per 0.02 degree 2-theta increment (continuous scan mode) over the range 2 degrees to 40 degrees 2-theta in theta-theta mode. The running time was 2 hours 6 minutes and 40 seconds. The instrument was equipped with a scintillation counter as detector. Control and data capture was by means of a Dell Optiplex 686 NT 4.0 Workstation operating with Diffract+ software.

The X-ray powder diffraction spectra for typical samples of the salts of (1) to (9) above are shown in the Figures hereinafter. It will be understood that the 2-theta values of the X-ray powder diffraction pattern may vary slightly from one machine to another or from one sample to another, and so the values quoted are not to be construed as absolute.

A further aspect of the present invention comprises processes for the preparation of the crystalline salts. The precise conditions under which the crystalline salts are formed may be empirically determined. The salts may be obtained by crystallisation under controlled conditions. Processes which have been found suitable are disclosed in the Examples hereinafter, and these are further independent aspects of the invention. For example, a process for the manufacture of the methylammonium salt (2) above comprises the addition of methylamine in a suitable solvent, such as water or methanol, to a cold, preferably freshly prepared solution of (E)-7-[4-(4-fluorophenyl)-6-isopropyl-2-[methyl (methylsulfonyl)amino]-pyrimidin-5-yl]-(3R,5S)-3,5-dihydroxyhept-6-enoic acid in a suitable solvent, such as a solvent comprising acetonitrile. For other crystalline salts, a cold, preferably freshly prepared solution of the heptenoic acid in a solvent comprising, for example, acetonitrile or ethyl acetate may be used and the appropriate amine or base may be added in the presence or absence of a solvent, dependent on the nature of the particular amine or base. Typically, after the amine or base is added, the mixture is stirred between ambient temperature and about 30° C., and the crystalline product isolated by filtration (after concentration and/or cooling as necessary). A solution of the heptenoic acid starting material in a suitable solvent may be obtained as described in the Examples hereinafter. A further aspect of the invention comprises a crystalline salt of the compound (E)-7-[4-(4-fluorophenyl)-6-isopropyl-2-[methyl (methylsulfonyl)amino]-pyrimidin-5-yl]-(3R,5S)-3,5-dihydroxyhept-6-enoic acid obtainable by the process described in Example 1, 2, 3, 4, 5, 6, 7, 8 or 9.

The utility of the salts of the invention as HMG CoA reductase inhibitors may be demonstrated by standard tests and clinical studies, including those described in EPA 521471. Typically the crystalline salts of the invention give an $IC_{50}$ value for inhibition of HMGCoA reductase activity in rat hepatic microsomes of 9 to 16 nM.

According to a further feature of the invention is a method of treating a disease condition wherein inhibition of HMG CoA reductase is beneficial which comprises administering to a warm-blooded mammal an effective amount of a crystalline salt as described above. The invention also relates to the use of the crystalline salts as described above in the manufacture of a medicament for use in a disease condition.

The compound of the invention may be administered to a warm-blooded animal, particularly a human, in need thereof for treatment of a disease in which HMG CoA reductase is implicated, in the form of a conventional pharmaceutical composition. Therefore in another aspect of the invention, there is provided a pharmaceutical composition comprising a crystalline salt as described above in admixture with a pharmaceutically acceptable diluent or carrier.

Such compositions may be administered in standard manner for the disease condition that it is desired to treat, for example by oral, topical, parenteral, buccal, nasal, vaginal or rectal administration or by inhalation. For these purposes a crystalline salt may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solution or suspensions or sterile emulsions. A preferred route of administration is oral. A crystalline salt will be administered to humans at a daily dose in, for example, the ranges set out in EPA 521471. The daily doses may be given in divided doses as necessary, the precise amount of the crystalline salt received and the route of administration depending on the weight, age and sex of the patient being treated and on the particular disease condition being treated according to principles known in the art.

According to a further feature of the invention, there is provided a process for the manufacture of a pharmaceutical composition containing a crystalline salt as described above as active ingredient, which comprises admixing a crystalline salt together with a pharmaceutically acceptable diluent or carrier.

According to a further feature of the invention there is provided the use of a crystalline salt as described above in the preparation of the amorphous calcium salt of (E)-7-[4-fluorophenyl)-6-isopropyl-2-[methyl(methylsulfonyl) amino]pyrimidin-5-yl]-(3R,5S)-3,5-dihydroxyhept-6-enoic acid. The crystalline methylammonium salt is particularly useful for this purpose. A further feature of the invention comprises a process for the manufacture of the amorphous calcium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid which comprises sequential reaction of the crystalline methylammonium salt with sodium hydroxide followed by a water soluble calcium salt, such as calcium chloride, under aqueous conditions.

The invention will now be illustrated by the following non-limiting Example.

EXAMPLE 1

A solution of methylamine in methanol (1.4 ml of a 40% solution) was added with stirring to a solution of (E)-7-[4-(4-fluorophenyl)-6-isopropyl-2-[methyl(methylsulfonyl) amino]pyrimidin-5-yl]-(3R,5S)-3,5-dihydroxyhept-6-enoic acid (obtained as described below) at −5° C. The mixture was stirred at 30° C. for 90 minutes and then cooled to 3° C. The crystalline product was collected by filtration, washed with acetonitrile and dried under vacuum at 40° C. to give methylammonium (E)-7-[4-(4-fluorophenyl)-6-isopropyl-2-[methyl(methylsulfonyl)amino]pyrimidin-5-yl]-(3R,5S)-3,5-dihydroxyhept-6-enoate (3.85 g; 87.9% yield) as white crystals. (The same crystalline salt was obtained when a 40% solution of methylamine in water (1.1 ml) was used). The X-ray powder diffraction spectra (XRD) for a typical sample of the crystalline methylammonium salt is shown in FIG. 2 hereinafter. The ten most prominent peaks in the XRD occur at about 2-theta=8.2, 12.3, 15.7, 16.5, 17.6, 18.7, 19.9, 21.0, 24.3 and 25.9°.

The solution of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid in acetonitrile used in Example 1 was obtained as follows:

(1) a mixture of methyl 2-amino-4-(4-fluorophenyl)-6-isopropyl-pyrimidine-5-carboxylate (19.0 g) (described in Japanese Patent Application No. 06-256318), sodium tert-pentoxide (22.95 g) and dimethoxyethane (190 ml) was stirred for 30 minutes at 25° C. The stirred mixture was cooled to −10° C. and methanesulfonyl chloride (8.4 ml) was added dropwise, maintaining the temperature of the mixture at −5° C. After 20 minutes, dimethyl sulfate (8.1 ml) was added and the mixture allowed to warm to 25° C. The mixture was stirred for one hour at 25° C. and a solution of sodium tert-pentoxide (1.91 g) in dimethoxyethane (10 ml) added. The mixture was stirred for one hour at 25° C. A solution of sodium chloride (13.3 g) in water (133 ml) was added and the mixture was stirred for 10 minutes at 25° C. The mixture was allowed to settle for 15 minutes and the lower aqueous phase was separated and discarded. Water (38 ml) was added to the remaining mixture and the mixture was stirred for 30 minutes at 25° C. The mixture was then heated to obtain a complete solution. The mixture was cooled slowly to 25° C. over one hour. The mixture was cooled to 0° C., stirred for one hour, and the suspended solid collected by filtration. The solid was washed with cold (0° C.) solution of 50:50 water/dimethoxyethane (20 ml). The solid was dried under vacuum at 60° C. to give methyl 4-(4-fluorophenyl)-6-isopropyl-2-[methyl(methylsulfonyl)amino]pyrimidine-5-carboxylate (Compound A; 19.35 g); $^1$HNMR (270 MHz, CDCl$_3$): 7.69(m,2H), 7.14(m,2H), 3.71, 3.60, 3.51 (3×s, 9H), 3.20 (m, 1H), 1.32 (d,6H).

(2) a stirred mixture of Compound A (12.0 g) in toluene (55 ml) was cooled to −10° C. and diisobutyl aluminium hydride (50 ml of a 1.5M solution in toluene) was added over two hours maintaining the temperature below 0° C. After addition, the mixture was stirred for 30 minutes at 0° C. Methanol (0.64 ml) was added to the mixture maintaining the temperature at 0° C. The mixture was then added over two hours to a stirred mixture of concentrated hydrochloric acid (23.3 ml), water (40.5 ml) and acetonitrile (24 ml) at 40° C., maintaining the temperature of the mixture at 40° C. After addition, the mixture was stirred at 40° C. for a further 30 minutes and then purged with nitrogen (to remove any isobutane). The mixture was cooled to 20° C. and allowed to stand for 20 minutes. The organic phase was separated and washed with a mixture of concentrated hydrochloric acid (0.7 ml) and water (30 ml). Acetonitrile (24 ml) was added to the organic phase and the mixture washed with a solution of sodium bicarbonate (0.038 g) in water (120 ml).

The organic phase was heated to 40° C., and then from 40° C. to 80° C. using a nitrogen purge. The mixture was concentrated by distillation at atmospheric pressure, collecting 54 ml of distillate. Acetonitrile (24 ml) was added to the concentrated solution and phosphorus tribromide (1.2 ml) was added with stirring, maintaining the temperature of the mixture at 20° C. After addition, the mixture was stirred at 20° C. for 30 minutes. The mixture was added to water (36 ml) over 30 minutes maintaining the temperature at 20° C. The mixture was stirred for 5 minutes and the organic phase separated. The organic phase was washed with a solution of sodium bicarbonate (0.027 g) in water (36 ml), followed by water (36 ml). The organic phase was distilled under reduced pressure until 29 ml of distillates was collected. The mixture was cooled to 60° C. and ethyl diphenylphosphinite (7.47 ml) was added. The mixture was stirred at 60° C. for 3 hours, then heated to reflux. Toluene (40 ml) was added and the mixture cooled to 0° C. over 2 hours. The product was collected by filtration, washed with cold toluene (10 ml) and dried under vacuum at 50° C. to give diphenyl [4-(4-fluorophenyl)-6-isopropyl-2-[methyl(methylsulfonyl) amino]pyrimidin-5-ylmethyl] phosphine oxide (Compound B;14.66 g); $^1$HNMR (CDCl$_3$, 270 MHz): 7.42 [m, 10H, P(C$_6$H$_5$)$_2$], 7.12 [m, 2H, Ar—H],6.92 [m, 2H, Ar—H], 3.92 [d,2H, CH$_2$P], 3.51, 3.46 (2×s, 6H, NCH$_3$ SO$_2$CH$_3$], 3.43 [hept., 1H, CH(CH$_3$)$_2$], 1.25 [d, 6H, CH(CH$_3$)$_2$]

(3) a mixture of Compound B (19.17 g) and THF (227 ml) were warmed briefly to 40° C. until a clear solution had formed then inerted by the sequential application of vacuum and nitrogen (5 cycles). The mixture was immersed in an acetone/CO$_2$ bath cooling the contents to −75° C. Sodium bis(trimethylsilyl)amide (37.4 ml of 1.0M solution in THF) was added to the reaction mixture over 10 minutes from a pressure equalising dropping funnel maintaining the temperature below −74° C. and forming a red solution of the anion. THF (10 ml) was rinsed through the dropping funnel into the mixture and the mixture stirred a further 1 hour at −76° C. forming a red suspension. Tert-butyl 2-[(4R,6S)-6-formyl-2,2-dimethyl-1,3-dioxan-4-yl] acetate (which may be obtained as described in European Patent 0319847) (80 ml of ~13.5% w/w toluene solution) was added in portions to the suspension over 20 minutes from a pressure equalising dropping funnel maintaining the temperature below −73° C. Toluene (20 ml) was rinsed through the dropping funnel into the mixture and the mixture stirred a further 15 minutes at −76° C. The chilling bath was lowered and the suspension allowed to warm to 10° C. over 1.5 hours. Glacial acetic acid (3.21 g) in water (15 g) was added in one portion raising the temperature to 18° C. and dissolving all solids and the mixture was stirred a further 5 minutes.

The mixture was concentrated by distillation at atmospheric pressure (jacket 110° C.) to a temperature of 94° C. collecting a total of 274 ml distillates. The concentrated mixture was cooled to 40° C., water (40 ml) was added and the mixture stirred for 5 minutes then allowed to settle for 15 minutes. The lower aqueous phase was discarded. Sodium hydrogen carbonate (2.99 g) in water (40 ml) was added and the mixture stirred for 5 minutes then allowed to settle for 15 minutes. The lower aqueous phase was discarded. Water (30 ml) was added and the mixture stirred for 5 minutes then allowed to settle for 15 minutes. The lower aqueous phase was discarded.

The organic phase was transferred to a distillation apparatus with toluene (20 ml) and concentrated by distillation at atmospheric pressure (jacket 125–130° C.) to a temperature of 116° C. collecting 85 ml distillates. Vacuum was applied (400-500 mbar) and a further 16.5 ml distillates collected to a temperature of 111° C. The vacuum was released and the concentrated mixture allowed to cool to 80° C. Warm MeOH (140 ml, 50° C.) was added with rapid stirring and the batch allowed to self-cool to 20° C. over 30 minutes during which time a solid was deposited. The suspension was further cooled to 2° C. for 30 minutes then the solid was collected by filtration on a sinter and pulled as dry as possible. The solid was washed with cold MeOH (60 ml, 2° C.) and again pulled as dry as possible then transferred to a vacuum oven and dried overnight (50° C., 200 mbar) to give Compound C. Compound C (5.0 g) in acetonitrile (70 ml) was heated at 40° C. and 0.01 M hydrochloric acid (19 ml) was added. The reaction mixture was heated to 40° C. for 5 hours. 1.0M Sodium hydroxide (9.5 ml) was added at 25° C., and the mixture was stirred for one hour. Sodium chloride was added and the mixture was cooled to −5° C. 1.0M Hydrochloric acid was added to adjust the pH of the mixture to pH 3.4–4.0. The aqueous phase was separated and the organic phase was diluted with acetonitrile (15 ml) then dried with anhydrous magnesium sulphate. Acetonitrile (20 ml) was added to give a solution of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid in acetonitrile.

EXAMPLE 2

Methylammonium (E)-7-[4-(4-fluorophenyl)-6-isopropyl-2-[methyl(methylsulfonyl)amino]-pyrimidin-5-yl]-(3R,5S)-3,5-dihydroxyhept-6-enoate (10 g) was added to acetonitrile (125 ml) and water (5 ml). The mixture was cooled to 5° C. and the pH adjusted to 3.7 with 1M hydrochloric acid in saturated brine (19 ml). The aqueous phase was separated off and the resulting solution was dried over anhydrous magnesium sulphate. Tris(hydroxymethyl) aminomethane (2.48 g) was added and the solution was allowed to warm to ambient temperature and stirred for 2 hours. The crystalline product was isolated by filtration at ambient temperature and dried at 30° C. under vacuum to give crystalline tris(hydroxymethyl)methylammonium (E)-7-[4-(4-fluorophenyl)-6-isopropyl-2-[methyl (methylsulfonyl)amino]pyrimidin-5-yl]-(3R,5S)-3,5-dihydroxyhept-6-enoate as white crystals. The X-ray powder diffraction spectra for a typical sample of the crystalline tris(hydroxymethyl)methylammonium salt is shown in FIG. 5 hereinafter. The ten most prominent peaks in the XRD occur at about 2-theta=7.9, 8.5, 10.2, 16.7, 18.4, 19.3, 19.8, 20.2, 21.5 and 24.9°.

EXAMPLE 3

Methylammonium (E)-7-[4-(4-fluorophenyl)-6-isopropyl-2-[methyl(methylsulfonyl)amino]-pyrimidin-5-yl]-(3R,5S)-3,5-dihydroxyhept-6-enoate (10 g) was added to ethyl acetate (125 ml) and water (30 ml). The mixture was cooled to 5° C. and 2M hydrochloric acid (9.5 ml) was added to obtain a two-phase solution. The aqueous phase was separated off and the organic phase was washed with water (30 ml) and dried over anhydrous magnesium sulphate. A solution of diethanolamine (3.1 ml) in ethyl acetate (5 ml) was added and the solution was allowed to warm to ambient temperature. The product was isolated by filtration at 0° C. to 5° C. and dried at 30° C. under vacuum to give diethanolammonium (E)-7-[4-(4-fluorophenyl)-6-isopropyl-2-[methyl(methylsulfonyl)amino]pyrimidin-5-yl]-(3R,5S)-3,5-dihydroxyhept-6-enoate (8.0 g) as white crystals. The X-ray powder diffraction spectra for a typical sample of the crystalline diethanolammonium salt is shown in FIG. 4 hereinafter. The ten most prominent peaks in the XRD occur at about 2-theta=9.9, 11.4, 16.1, 18.0, 18.7, 19.0, 20.6, 22.9, 24.3 and 25.0°.

EXAMPLE 4

Figure 1:
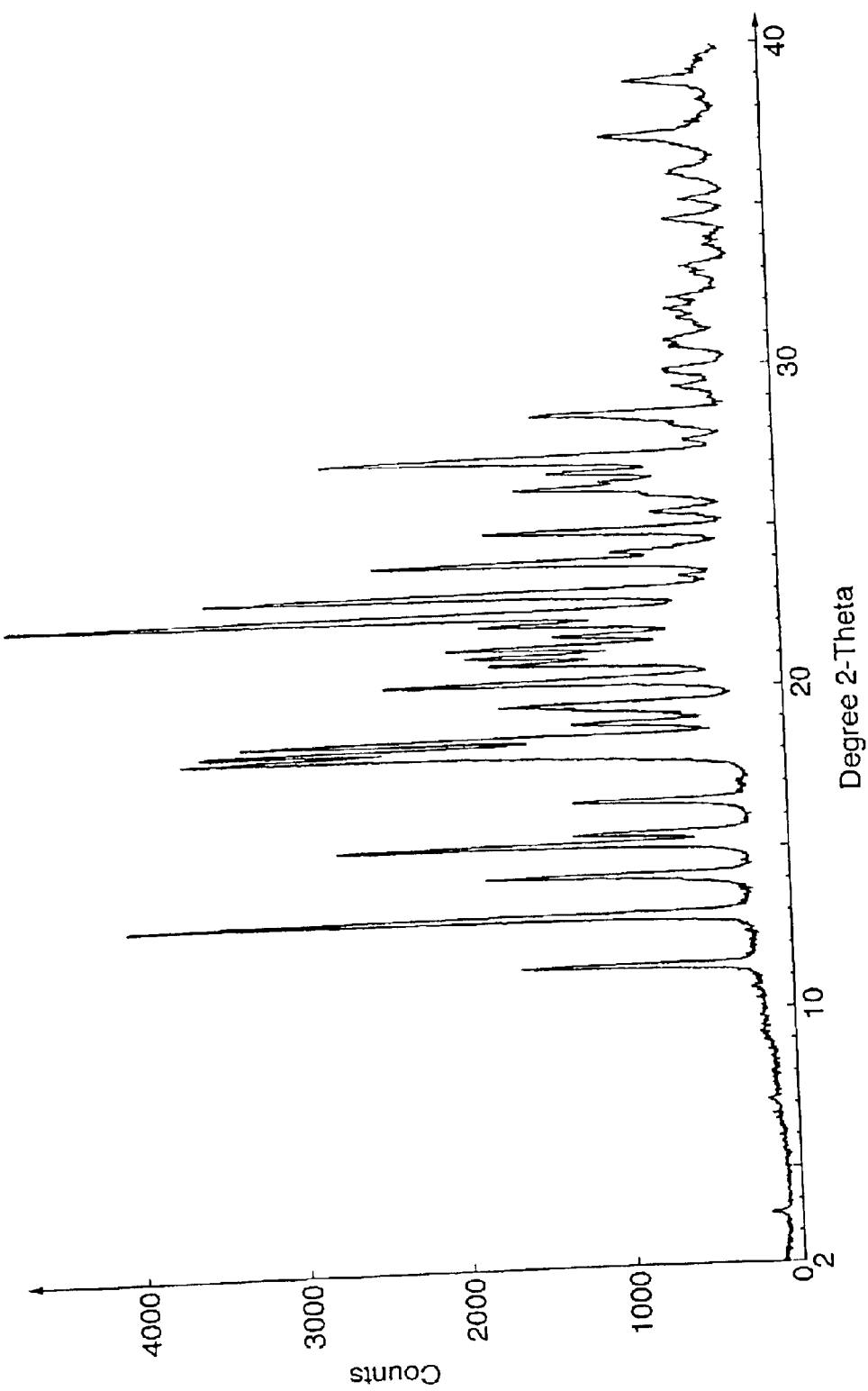

Methylammonium (E)-7-[4-(4-fluorophenyl)-6-isopropyl-2-[methyl(methylsulfonyl)amino]-pyrimidin-5-yl]-(3R,5S)-3,5-dihydroxyhept-6-enoate (10 g) was added to ethyl acetate (125 ml). The mixture was cooled to 5° C. and 1M hydrochloric acid in saturated brine (20 ml) was added, followed by water (30 ml) to obtain a two-phase solution. The aqueous phase was separated off and the organic phase was washed with water (30 ml) and dried over anhydrous magnesium sulphate. Aqueous ammonia (1.7 ml) was added, followed by ethyl acetate (80 ml), and the solution was concentrated under vacuum and diluted with ethyl acetate (60 ml). The mixture was stirred at 0° C. to 5° C. for 90 minutes and the product was isolated by filtration and dried at 30° C. under vacuum to give ammonium (E)-7-[4-(4-fluorophenyl)-6-isopropyl-2-[methyl(methylsulfonyl) amino]-pyrimidin-5-yl]-(3R,5S)-3,5-dihydroxyhept-6-enoate (6.33 g) as white crystals. The X-ray powder diffraction spectra for a typical sample of the crystalline ammonium salt is shown in FIG. 1 hereinafter. The ten most prominent peaks in the XRD occur at about 2-theta=12.9, 15.2, 18.0, 18.2, 18.5, 20.2, 22.4, 23.0, 24.0 and 27.2°.

EXAMPLE 5

Methylammonium (E)-7-[4-(4-fluorophenyl)-6-isopropyl-2-[methyl(methylsufonyl)amino]-pyrimidin-5-yl]-(3R,5S)-3,5-dihydroxyhept-6-enoate (10 g) was added to ethyl acetate (125 ml) and water (30 ml). The mixture was cooled to 5° C. and 2M hydrochloric acid (9.5 ml) was added to obtain a two-phase solution. The aqueous phase was separated off and the organic phase was washed with water (30 ml) and dried over anhydrous magnesium sulphate. Lithium hydroxide monohydrate (0.9 g) and water (3 ml) was added and the solution was concentrated under vacuum then diluted with ethyl acetate (100 ml). The product was isolated by filtration at 0° C. to 5° C. and dried at 30° C. under vacuum to give lithium (E)-7-[4-(4-fluorophenyl)-6-isopropyl-2-[methyl(methylsulfonyl)amino]pyrimidin-5-yl]-(3R,5S)-3,5-dihydroxyhept-6-enoate (8.23 g) as white crystals. The X-ray powder diffraction spectra for a typical sample of the crystalline lithium salt is shown in FIG. 8 hereinafter. The ten most prominent peaks in the XRD occur at about 2-theta=10.2, 11.0, 16.4, 17.0, 19.3, 19.8, 20.4, 20.9, 21.5 and 28.0°.

EXAMPLE 6

A solution of sodium (E)-7-[4-(4-fluorophenyl)-6-isopropyl-2-[methyl(methylsulfonyl)amino]pyrimidin-5-yl]-(3R,5S)-3,5-dihydroxyhept-6-enoate in aqueous acetonitrile (11 ml) containing sodium chloride (1.4 g) was cooled to −5° C. and the pH adjusted to 3.4 to 4 with 1M hydrchloric acid. The aqueous phase was separated off and the organic phase was filtered through anhydrous magnesium sulphate. Acetonitrile (14 ml) was added to the organic phase and aqueous ethylamine (0.21 ml) was added. The solution was heated to 30° C. and held at this temperature for 90 minutes. The product was isolated by filtration at 0° C. and dried at 35° C. under vacuum to give ethylammonium (E)-7-[4-(4-fluorophenyl)-6-isopropyl-2-[methyl(methylsulfonyl)amino]pyrimidin-5-yl]-(3R,5S)-3,5-dihydroxyhept-6-enoate (0.7 g) as white crystals. The X-ray powder diffraction spectra for a typical sample of the crystalline ethylammonium salt is shown in FIG. 3 hereinafter. The ten most prominent peaks in the XRD occur at about 2-theta=8.6, 15.9, 16.9, 18.4, 18.7, 19.7, 20.8, 23.3, 23.8 and 25.8°.

EXAMPLE 7

A solution of sodium (E)-7-[4-(4-fluorophenyl)-6-isopropyl-2-[methyl(methylsulfonyl)amino]pyrimidin-5-yl]-(3R,5S)-3,5-dihydroxyhept-6-enoate in aqueous acetonitrile (40 ml) was cooled to −5° C. and 1M hydrochloric acid (9.5 ml) containing sodium chloride (7.1 g) was added to adjusted the pH to 3.8. The aqueous phase was separated off and acetonitrile (70 ml) was added to the organic phase. Benzylamine (1.4 ml) was added and the solution was heated to 30° C. and held at this temperature for 90 minutes. The product was isolated by filtration at 0° C. and dried at 35° C. under vacuum to give benzylammonium (E)-7-[4-(4-fluorophenyl)-6-isopropyl-2-[methyl(methylsulfonyl)amino]pyrimidin-5-yl]-(3R,5S)-3,5-dihydroxyhept-6-enoate (4.4 g) as white crystals. The X-ray powder diffraction spectra for a typical sample of the crystalline benzylammonium salt is shown in FIG. 6 hereinafter. The ten most prominent peaks in the XRD occur at about 2-theta=6.1, 6.7, 16.8, 17.6, 18.1, 19.3, 21.1, 21.9, 23.0 and 26.8°.

EXAMPLE 8

A solution of sodium (E)-7-[4-(4-fluorophenyl)-6-isopropyl-2-[methyl(methylsulfonyl)amino]pyrimidin-5-yl]-(3R,5S)-3,5-dihydroxyhept-6-enoate in aqueous acetonitrile (11 ml) containing sodium chloride (1.4 g) was cooled to −5° C. and the pH adjusted to 3.4 to 4 with 1M hydrochloric acid. The aqueous phase was separated off and the organic phase was filtered through anhydrous magnesium sulphate. Acetonitrile (14 ml) was added to the organic phase and 4-methoxybenzylamine (0.34 ml) was added. The solution was heated to 30° C. and held at this temperature for 60 minutes. The product was isolated by filtration at 0° C. and dried at ambient temperature under vacuum to give 4-methoxybenzylammonium (E)-7-[4-(4-fluorophenyl)-6-isopropyl-2-[methyl(methylsulfonyl)-amino]pyrimidin-5-yl]-(3R,5S)-3,5-dihydroxyhept-6-enoate (0.65 g) as white crystals. The X-ray powder diffraction spectra for a typical sample of the crystalline 4-methoxybenzylammonium salt is shown in FIG. 7 hereinafter. The ten most prominent peaks in the XRD occur at about 2-theta=14.2, 15.1, 17.5, 18.8, 19.7, 20.1, 20.7, 21.5, 23.7 and 24.5°.

The aqueous acetonitrile solution of sodium (E)-7-[4-(4-fluorophenyl)-6-isopropyl-2-[methyl(methylsulfonyl) amino]pyrimidin-5-yl]-(3R,5S)-3,5-dihydroxyhept-6-enoate, used in Examples 6, 7 and 8, was obtained as follows:

Compound C (obtained in Example 1, part (3)) (5.0 g) in acetonitrile (35 ml) was heated to 40° C. and 0.02M hydrochloric acid (9.5 ml) was added. The reaction mixture was heated at 40° C. for 4 hours. 1.0M Sodium hydroxide (9.5 ml) was added at 25° C., and the mixture was stirred for 60 minutes to give a solution of the sodium salt in aqueous acetonitrile.

EXAMPLE 9

1.0M Sodium hydroxide solution (26.3 ml) was added to a stirred solution of methylammonium (E)-7-[4-(4-fluorophenyl)-6-isopropyl-2-[methyl(methylsulfonyl) amino]-pyrimidin-5-yl]-(3R,5S)-3,5-dihydroxyhept-6-enoate (15 g) in water (106 ml) at ambient temperature. A solution of magnesium sulphate (4.3 g) in water (26 ml) was added over 20 minutes and a solid precipitated. The solid was collected by filtration, washed with water (20 ml) and dried under vacuum at 40° C. (7.7 g). A mixture of the solid (5.8 g) and water (50 ml) was heated to 38° C. and diluted with water (35 ml). The mixture was stirred at ambient temperature for 4 hours and then allowed to stand for 66 hours. The solid was collected by filtration after diluting with water (30 ml). The product was dried at 35° C. under vacuum to give magnesium (E)-7-[4-(4-fluorophenyl)-6-isopropyl-2-[methyl(methylsulfonyl)amino]-pyrimidin-5-yl]-(3R,5S)-3,5-dihydroxyhept-6-enoate (4.68 g) as white crystals. The X-ray powder diffraction spectra for a typical sample of the crystalline magnesium salt is shown in FIG. 9 hereinafter. The ten most prominent peaks in the XRD occur at about 2-theta=11.5, 14.5, 16.3, 16.8, 18.0, 19.1, 19.8, 21.8, 22.6 and 23.0°.

EXAMPLE 10

Sodium hydroxide (8% w/w aqueous solution; 5.44 ml) was added to a stirred mixture of the methylammonium salt obtained in Example 1 (6.0 g) in degassed water (30 ml) at 20° C. and the mixture was stirred for one hour. The mixture was filtered and concentrated under reduced pressure at 40° C. until 24 ml of distillate collected. Water (24 ml) was added and the mixture again concentrated under reduced pressure at 40° C. until 24 ml of distillate collected. Water (30 ml) was added and a solution of calcium chloride dihydrate (1.03 g) in water (6 ml) was added dropwise at 20° C. The mixture was stirred for 45 minutes and the resultant solid filtered. The solid was washed with water (36 ml) and dried under vacuum at 40° C. to give non-crystalline calcium salt of (E)-7-[4-(4-fluorophenyl)-6-isopropyl-2-[methyl (methylsulfonyl)amino]pyrimidin-5-yl](3R,5S)-3,5-dihydroxyhept-6-enoic acid.

What is claimed is:

1. A crystalline salt of the compound (E)-7-[4-(4-fluorophenyl)-6-isopropyl-2-[methyl(methylsulfonyl)amino]pyrimidin-5-yl]-(3R,5S)-3,5-dihydroxyhept-6-enoic acid, wherein the salt is an ammonium, methylammonium, ethylammonium, diethanolammonium, tris(hydroxymethyl)methylammonium, benzylammonium, 4-methoxybenzylammonium, lithium or magnesium salt.

2. A crystalline salt as claimed in claim 1 which is a crystalline ammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=12.9, 15.2, 18.0, 18.2, 18.5, 20.2, 22.4, 23.0, 24.0 and 27.2°.

3. A crystalline salt as claimed in claim 1 which is a crystalline methylammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=8.2, 12.3, 15.7, 16.5, 17.6, 18.7, 19.9, 21.0, 24.3 and 25.9°.

4. A crystalline salt as claimed in claim 1 which is a crystalline ethylammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=8.6, 15.9, 16.9, 18.4, 18.7, 19.7, 20.8, 23.3, 23.8 and 25.8°.

5. A crystalline salt as claimed in claim 1 which is a crystalline diethanolammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=9.9, 11.4, 16.1, 18.0, 18.7, 19.0, 20.6, 22.9, 24.3 and 25.0°.

6. A crystalline salt as claimed in claim 1 which is a crystalline tris(hydroxymethyl)methylammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=7.9, 8.5, 10.2, 16.7, 18.4, 19.3, 19.8, 20.2, 21.5 and 24.9°.

7. A crystalline salt as claimed in claim 1 which is a crystalline benzylammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=6.1, 6.7, 16.8, 17.6, 18.1, 19.3, 21.1, 21.9, 23.0 and 26.8°.

8. A crystalline salt as claimed in claim 1 which is a crystalline 4-methoxybenzylammonium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=14.2, 15.1, 17.5, 18.8, 19.7, 20.1, 20.7, 21.5, 23.7 and 24.5°.

9. A crystalline salt as claimed in claim 1 which is a crystalline lithium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=10.2, 11.0, 16.4, 17.0, 19.3, 19.8, 20.4, 20.9, 21.5 and 28.0°.

10. A crystalline salt as claimed in claim 1 which is a crystalline magnesium salt of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid having an X-ray powder diffraction pattern with specific peaks at 2-theta=11.5, 14.5, 16.3, 16.8, 18.0, 19.1, 19.8, 21.8, 22.6 and 23.0°.

11. A pharmaceutical composition comprising a crystalline salt as claimed in any of claims 1 to 10 in admixture with a pharmaceutically acceptable diluent or carrier.

12. A process for the manufacture of a crystalline salt as claimed in any one of claims 2 to 9 which comprises addition of the appropriate amine or base to a solution of (E)-7-[4-(4-fluorophenyl)-6-isopropyl-2-[methyl(methylsulfonyl)amino]pyrimidin-5-yl]-(3R,5S)-3,5-dihydroxyhept-6-enoic acid in acetonitrile or ethyl acetate.

* * * * *